United States Patent
MacLauchlan et al.

[11] Patent Number: 6,122,969
[45] Date of Patent: Sep. 26, 2000

[54] MAIN BANG RECOVERY EMAT

[75] Inventors: Daniel T. MacLauchlan; Jimmy W. Hancock, both of Lynchburg, Va.

[73] Assignee: McDermott Technology, Inc., New Orleans, La.

[21] Appl. No.: 09/138,620

[22] Filed: Aug. 24, 1998

[51] Int. Cl.[7] .................................................. G01N 29/24
[52] U.S. Cl. ........................................................ 73/643
[58] Field of Search ..................................... 73/643, 627

[56] References Cited

U.S. PATENT DOCUMENTS

| | | | |
|---|---|---|---|
| 2,277,037 | 3/1942 | Clark et al. ................................. | 73/51 |
| 3,357,556 | 12/1967 | Martner et al. ........................... | 209/73 |
| 3,553,636 | 1/1971 | Baird ......................................... | 340/1 |
| 3,802,252 | 4/1974 | Hayward et al. .......................... | 73/52 |
| 3,832,885 | 9/1974 | Hayward et al. .......................... | 73/52 |
| 3,913,383 | 10/1975 | Kreula et al. .............................. | 73/52 |
| 4,208,915 | 6/1980 | Edwards ................................... | 73/620 |
| 4,384,476 | 5/1983 | Black et al. ............................... | 73/61 |
| 4,399,514 | 8/1983 | Hamasaki et al. ..................... | 364/558 |
| 4,408,493 | 10/1983 | Peterson ................................... | 73/643 |
| 4,434,663 | 3/1984 | Peterson et al. .......................... | 73/643 |
| 4,580,448 | 4/1986 | Skrgatic ................................... | 73/290 |
| 4,821,573 | 4/1989 | Nagata et al. ............................ | 73/597 |
| 4,848,924 | 7/1989 | Nuspl et al. ............................. | 374/119 |
| 5,167,157 | 12/1992 | Wertz et al. ............................... | 73/627 |
| 5,372,042 | 12/1994 | Jarman et al. ............................ | 73/588 |
| 5,439,157 | 8/1995 | Geier et al. ............................... | 73/643 |
| 5,449,958 | 9/1995 | MacLauchlan et al. .................. | 73/643 |
| 5,608,164 | 3/1997 | MacLauchlan ........................... | 73/599 |
| 5,837,898 | 11/1998 | MacLauchlan ........................... | 73/599 |

FOREIGN PATENT DOCUMENTS

| | | | |
|---|---|---|---|
| 56-21058 | 2/1981 | Japan ....................................... | 73/643 |
| 57-165761 | 10/1982 | Japan ....................................... | 73/643 |
| 58-92825 | 6/1983 | Japan ....................................... | 73/290 |

OTHER PUBLICATIONS

Maxfield, B.W., A. Kuramoto & J.K. Hulbert, "Evaluating EMAT Designs for Selected Applications", *Materials Evaluation*, 45, Oct. 1987. pp. 1166–1183.

Thompson, R.B. & C.F. Vasile, "An elastic–wave ellipsometer for measurement of material property variations", *Appl. Phys. Lett.*, 34(2), Jan. 15, 1979. pp. 128–130.

B. W. Maxfield and C. M. Fortunko, The Design and Use of Electromagnetic Acoustic Wave Transducers (EMATs), *Materials Evaluation*/41/Nov. 1983, pp. 1399–1408.

*Primary Examiner*—John E. Chapman
*Attorney, Agent, or Firm*—R. J. Edwards; Eric Marich; R. C. Baraona

[57] ABSTRACT

An EMAT arrangement utilizes separate transmitter and receiver EMATs which may each be connected to a tuning capacitor by a stripline cable. An electrostatic shield may also be provided between the coils and the coils can be offset from each other by ½ the pitch distance of sections in the coil. This reduces the duration of main bang, thus making it possible for the EMAT arrangement to detect structures which are very close to the coils.

6 Claims, 2 Drawing Sheets

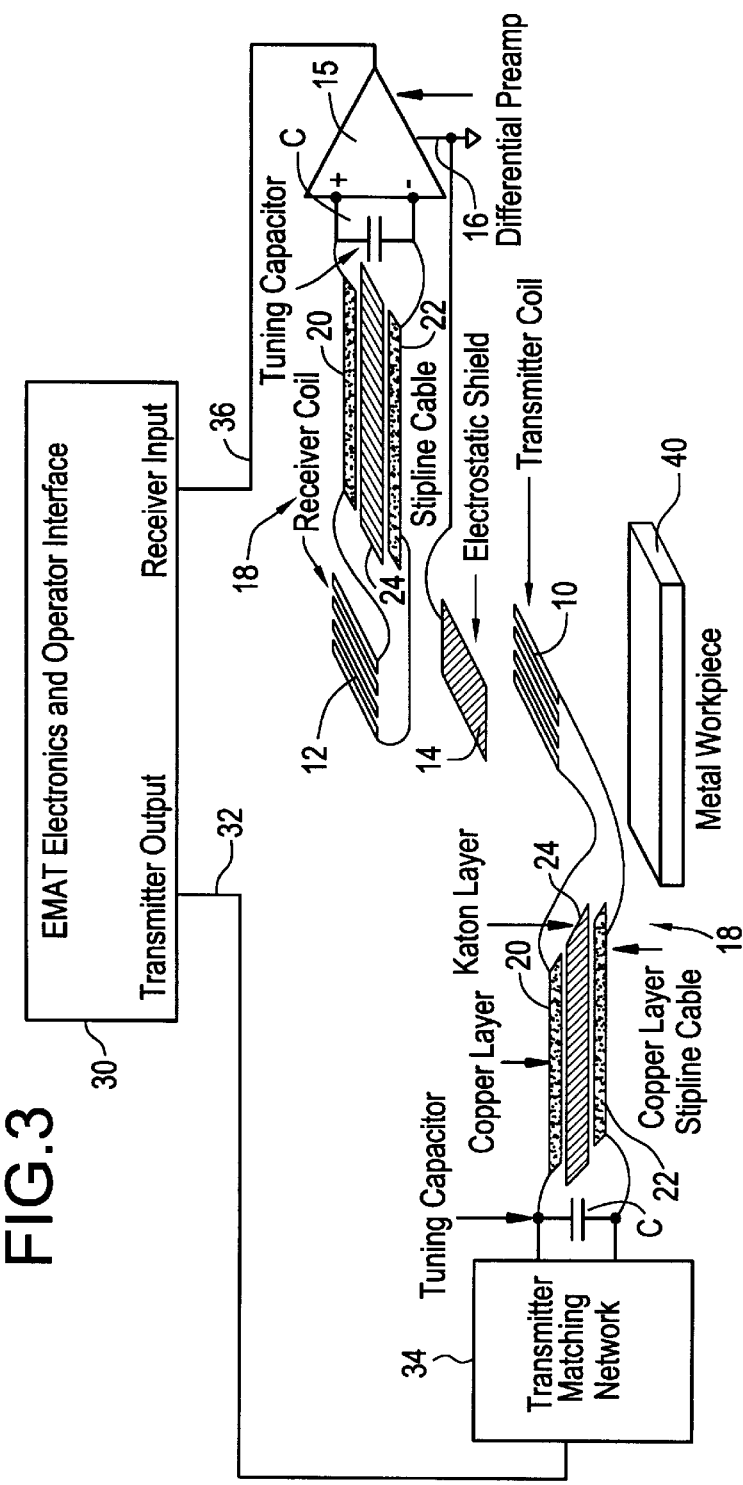

MAIN BANG RECOVERY EMAT

FIELD AND BACKGROUND OF THE INVENTION

The present invention relates in general to the use of electromagnetic acoustic transducers (EMATs) for testing materials and, in particular, to a new and useful method and apparatus for performing non-destructive testing using EMATs which avoids the problem of "main bang," that is, the overloading of the EMAT receiver by the electrical interference created by the high energy transmitter pulse.

In most cases, prior art EMAT testing systems use the same EMAT coil to transmit waves and to receive reflected waves. Resistance was added to the EMAT coil, in some cases, in order to reduce the Q of the tuned circuit, reducing the duration of the main bang or overload signal, but at the same time reducing signal amplitude and signal-to-noise ratio. In other cases separate non-overlapping coils were used to transmit and receive. This can cause problems because the coils are not at the same location for transmitting and receiving.

When performing nondestructive testing using EMATs, there is typically a region adjacent the EMAT from which no reflections can be received due to main bang. Main bang is a large signal in the receiver output created by the transmitter pulse. This is such a large signal that it completely overloads the receiver, preventing it from detecting any reflections during this time. The duration of the main bang includes the length of the transmit pulse, and a period of time immediately after transmitting, during which the transmit pulse decays to a level small enough so that it no longer interferes with the detection of reflections. The duration of the main bang is a significant impediment for many potential applications of EMATs at the present time.

SUMMARY OF THE INVENTION

An object of the present invention is to reduce the duration of the main bang in an EMAT based system. The method and apparatus according to the invention has been tested and reduces main bang duration by a factor of two.

Another object of the present invention is to achieve reduction of main bang by using separate coils for transmitting and receiving EMAT waves through the work piece to be tested, by minimizing the coupling between these two coils, and by separating and isolating the transmitter and receiver electronics. This reduces Q of the tuned circuits used to match the EMAT coils to the EMAT electronics.

By constructing an EMAT with separate coils for transmitting and receiving, and by adding an electrostatic shield between the transmitter coil and the receiver coil, capacitive coupling of the large transmit pulse to the receiver coil is greatly reduced. The electrostatic shield can be formed by using a very thin layer of high resistivity nonmagnetic metal such as titanium, or a highly conductive nonmagnetic metal such as copper with gaps etched in the layer to prevent eddy currents from being produced in the shield layer which would attenuate the actual EMAT signal. For meander coil EMATs, offsetting the transmitter EMAT coil and receiver EMAT coil by half the wire-to-wire spacing or by a quarter wavelength of the wave, minimizes the magnetic coupling between these two coils, again reducing the duration of the main bang.

In order to optimize power transfer to the EMAT coil, typically, the inductance of the EMAT coil is resonated by placing a capacitor in parallel with it. By selecting the capacitor so that it resonates with the coil inductance at the desired frequency of operation, the impedance becomes real, allowing the maximum transfer of power to the resistance of the EMAT coil. Often a considerable length of cable is connected between the EMAT coil and the matching network. Typically these cables add considerable inductance and little additional resistance to the EMAT circuit. This tends to raise the Q, which is defined as the inductive impedance ($Z_L = 2\pi fL$) divided by the resistance of the circuit ($Q = Z_L/R$). Higher Q results in the tuned circuit "ringing" longer after the excitation drive has been removed, causing increased mainbang duration.

By placing the tuning capacitor as close as possible to the EMAT coil, and using a printed flex circuit stripline to connect the EMAT coil to the capacitor, the additional inductance is minimized. A flexible stripline is constructed by placing two narrow strips of thin copper on either side of a thin flexible plastic such as Kapton® (a trademark for a polyamide plastic). For example the copper may be 0.25" wide by 0.001" thick and the Kapton® plastic 0.001" thick. This provides much lower Q resonant circuits, which results in reduced main bang duration while providing the same or somewhat improved signal-to-noise (by reducing the resistance of the connecting cable). By using a combination of these techniques the main bang duration can be substantially reduced.

Testing indicates that the main bang duration can be reduced by as much as a factor of two using this technique as opposed to using the same coil for both transmitting and receiving. In addition, this technique has been found to be very effective at reducing sensitivity to electrical noise. The electrostatic shield serves to prevent electrical noise on the part from being capacitively coupled to the receiver EMAT coil.

As alternatives, the coils and shield could be constructed using printed circuit techniques or manually constructed using hand wound coils. The electrostatic shield could be a copper layer with narrow gaps in the copper to prevent the generation of eddy currents in the copper layer so as to prevent attenuating the magnetically coupled EMAT signals.

Accordingly, one aspect of the present invention is to provide an EMAT arrangement which comprises at least one EMAT coil having opposite coil ends, a tuning capacitor and a stripline cable connected between the coil ends and the capacitor for minimizing losses between the coil and the capacitor.

Another aspect of the present invention is to provide separate transmitter and receiver EMATs which are separated from each other by an electrostatic shield.

Yet another aspect of the present invention is to provide such an arrangement where the separate coils each have multiple sections which are separated by a pitch distance, with the coils being offset from each other by one-half the pitch distance or by one-quarter of the wavelength of the wave meant to be transmitted from the transmitter coil.

Yet still another aspect of the present invention is to provide an EMAT arrangement which includes a preamp connected to the receiver EMAT coil, and a matching network between the EMAT electronics and the transmitter EMAT coil for producing the acoustic signals.

The various features of novelty which characterize the invention are pointed out with particularity in the claims annexed to and forming a part of this disclosure. For a better understanding of the invention, its operating advantages and specific benefits attained by its uses, reference is made to the accompanying drawings and descriptive matter in which a preferred embodiment of the invention is illustrated.

BRIEF DESCRIPTION OF THE DRAWINGS

In the drawings:

FIG. 3 is a schematic exploded view of an EMAT arrangement according to the present invention; and FIG. 4 is a side elevational view of a receiver and a transmitter EMAT with an electrostatic shield therebetween, according to the present invention.

DESCRIPTION OF THE PREFERRED EMBODIMENTS

Figure 1:
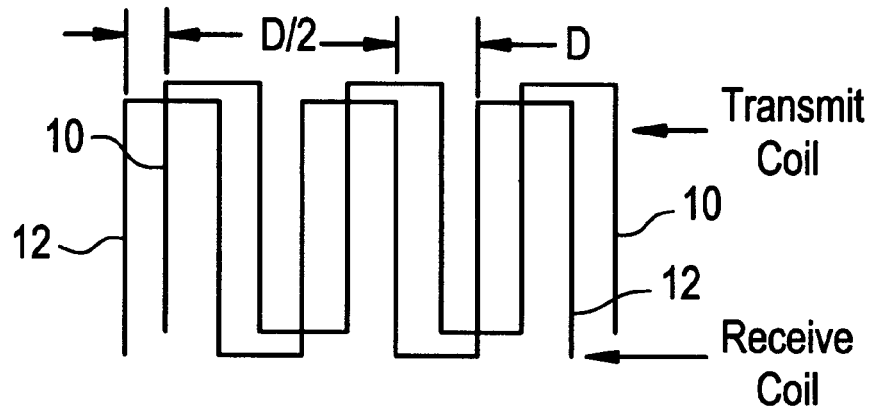
FIG. 1 is a top schematic plan view of a pair of EMAT coils offset from each other in accordance with the present invention.

Referring to the drawings generally, wherein like reference numerals represent the same or functionally similar elements throughout the several drawings, and to FIG. 1 in particular, the invention embodied therein comprises an improved EMAT arrangement which uses various techniques for reducing the main bang duration so that the EMAT arrangement can be used for inspecting structures that are very close to the EMAT coils.

The invention has been tested and incorporated into a 2.25 MHz EMAT used for detecting longitudinal defects in tubular products. The main bang duration was reduced from more than 20 microseconds to less than 11 microseconds. The electrostatic shield also eliminates EMI pickup from the part being tested.

Figure 2:
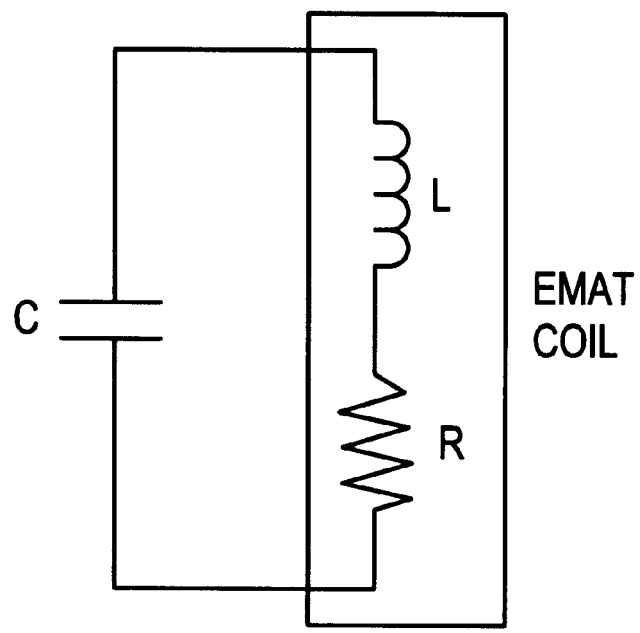
FIG. 2 is an electric equivalent circuit of an EMAT coil and a tuning capacitor according to the present invention.

EMATs are inefficient ultrasound generators and receivers. Typically a 1000 volt tone burst pulse applied to the EMAT coil might result in only 1 millivolt of received signal. In order to obtain signals with sufficient signal to noise, it is necessary to use very large transmit pulses, and very sensitive receivers. It is also necessary to carefully tune and match the EMAT coils to the transmitter and receiver electronics, to insure maximum power transfer. Electrically, the EMAT coil appears to be an inductor L in series with a resistor R as illustrated in FIG. 2. The maximum signal-to-noise ratio is obtained when the transmitter current in the EMAT coil is maximized, which occurs when the power transferred from the transmitter electronics to the EMAT coil resistance is maximized, $P=I^2R$, where P=power, I is the current in the EMAT coil, and R is the coil resistance. In order to maximize the power transfer the inductance of the EMAT coil must be neutralized and the impedance transformed to match the resistance for maximum power generation by the transmitter electronics. Typically, this is done by connecting a capacitor C in parallel with the EMAT coil such that it resonates the EMAT circuit at the desired operating frequency. The resonant frequency $f_0$ for such a circuit is given approximately by:

$$f_0 \approx 1/(2\pi(LC)^{1/2}).$$

The tuned circuit will have an impedance Z that is real (appears to be resistive) at the resonant frequency $f_0$ and have a value given by:

$$Z \approx (2\pi f_0 L)^2/R.$$

where R is the resistance of the EMAT coil. This impedance is matched to the transmitter using a transformer, such that the transformed impedance matches the optimum transmitter load resistance. By resonating the EMAT coil with a capacitor and matching it with a transformer, nearly 100% of the transmitter power can be delivered to the EMAT coil resistance.

A side effect of the tuned circuit however is that the circuit continues to oscillate at the resonant frequency for some time after the transmit pulse has been turned off. This oscillation decays in amplitude exponentially. The rate of decay is determined by the Q of the resonant circuit. The higher the Q, the longer the resonant circuit rings. The lower the Q, the faster it decays. The Q is given by:

$$Q=2\pi f_0 L/R.$$

At a given frequency, the Q is determined by the ratio of the inductance of the circuit divided by the resistance of the circuit. The amplitude of the voltage oscillation decays at a rate given by:

$$V(t)=V_0 e^{-tR/2L}=V_0 e^{-t\omega/2Q}$$

where:

$$\omega=2\pi f_0.$$

The rate of decay is increased by going to higher frequencies and lower Q values, decreasing the duration of the main bang. Assuming use of the same EMAT coil to transmit and receive, one can estimate the duration of the main bang. The duration of the main bang is the length of the transmit pulse plus the time it takes for the voltage to decay below the noise floor of the receiver. When the amplitude of the transmitter oscillation falls below the noise floor of the receiver it is no longer detectable. The duration of the main bang may then be expressed as:

$$t_{mainbang}=t_{transmit}+2Q/\omega \ln (V_{transmit}/V_{noise}).$$

For example a typical EMAT system operates with the following parameters; a 1000 volt peak to peak transmit tone burst pulse, 4 microsecond transmit pulse width, frequency of 2 MHz, Q of 5, and a receiver noise floor of 2 microvolts peak to peak. Using these values a main bang duration time of 20 microseconds is calculated. This agrees well with actual main bang durations observed during testing. For shear wave testing this corresponds to a dead zone of approximately 1¼".

By using separate coils for transmitting and receiving the voltage induced on the receiver coil by the transmitter pulse can be greatly reduced. The majority of EMAT applications utilize meander coils. FIG. 1 shows an EMAT meander coil arrangement in which the transmitter coil 10 and the receiver coil 12 are offset by ¼ wavelength (P½). Because the direction of the current in the transmitter EMAT coil alternates in direction, offsetting the receiver coil ¼ wavelength reduces the electromagnetic coupling between the coils to near zero. By placing a very thin high resistivity metal shield 14 in FIG. 4, between the two coils 10 and 12, and grounding it to a common 16 at the preamplifier 15 as shown in FIG. 3, the capacitive coupling between the two coils can be nearly eliminated.

This results in large attenuation of the signal induced on the receiver coil 12 by the transmitter coil 10. A 60 dB (factor of 1000) reduction in the induced transmitter signal would result in a main bang duration from our previous example of 14.4 microseconds. This is a substantial reduction in main bang dead zone.

A second method for reducing the duration of the main bang according to the invention is to decrease the Q of the tuned EMAT circuit. One method of doing this is to add resistance in series with the EMAT coil. This has the desired effect of reducing the Q but also reduces the signal-to-noise ratios that can be obtained. However, in many applications, some loss in signal-to-noise can be tolerated in order to obtain reduced main bang duration. In most applications a cable is used to connect the EMAT matching and tuning electronics to the EMAT coils. The inductance and resistance of the cable add to the resistance and inductance of the EMAT coil. However, it should be noted any resistance contributed by the cable reduces the power delivered to the EMAT coil. The added inductance of the cable can be substantial, in some cases, several times more than the inductance of the EMAT coil itself. This tends to raise the Q of the tuned circuit resulting in increased main bang duration. Experiments have shown that by tuning the EMAT as close to the EMAT coil as possible, Q values of two or less can be obtained.

A very low resistance and inductance cable can be obtained using stripline construction illustrated in FIG. 3. A stripline 18 is formed by running two wide traces 20 and 22 on opposite sides of a thin flexible plastic layer 24, directly across from each other. By using a short run of stripline 18 to connect the EMAT coil 10 or 12 to the tuning capacitor C, very little additional inductance and resistance is added to that of the EMAT coil. This allows efficient transfer of power to the EMAT coil and keeps the Q of the resonant circuit as low as possible without sacrificing signal to noise ratio. Using a Q value of 2, and assuming 60 dB attenuation of the transmitter signal induced on the receiver coil, a main bang duration value of 8.2 microseconds is calculated. This is a very significant improvement in main bang duration, corresponding to a dead zone of only ½" for shear wave testing. The known EMAT electronics 30 generates a transmitter signal at its output 32 which is supplied to the transmitter coil 10 through a matching network 34 and the cable 18. The reflected wave at coil 12 produces a signal that is supplied along the other cable 18, to the preamp 15, and its outlet which is connected to the receiver input 36 of electronics 30.

In order to test the invention, an experimental setup was assembled using standard laboratory EMAT electronics 30. A separate EMAT transmitter coil 10 and receiver coil 12 were assembled. Separate electronics enclosures 34 were used for matching the EMAT transmitter coil 10 and preamp 15 used for the receiver EMAT coil 12. By separating the two EMAT coils by a large distance, a check could be performed to verify that there was no significant coupling of the transmit pulse to the preamp and receiver circuits through the electronics. This confirmed that the source of main bang was coupling between the transmit coil and receiver coil.

The coupling between two meander coil EMATs was tested. A meander coil EMAT was attached to an aluminum plate using adhesive. The tracking generator output of a spectrum analyzer was connected to one of the EMAT coils via a 1:1 RF transformer for isolation. A second identical EMAT coil was placed above the first EMAT coil and connected to the high impedance input of the spectrum analyzer via a 1:1 transformer. All measurements were made at 2 MHz. A 6.3 mV r.m.s. signal was generated across the terminals of the transmitter EMAT coil. With the two coils aligned with one exactly above the other a 2.32 mV r.m.s. signal was measured at the terminals of the receiver EMAT coil. By moving the receiver EMAT coil with respect to the transmitter EMAT coil, a null in the receiver coil voltage could be obtained. This null was fairly sharp and occurred when the two EMAT coils were aligned as shown in FIG. 1 with straight segments of the receiver EMAT coil exactly in between the straight segments of the transmitter EMAT coil. When nulled, the signal from the receiver EMAT coil was measured to be 14 microvolts r.m.s. This is 450 times less than the voltage across the transmitter coil.

Using the principles outlined above, an EMAT coil was designed for use as part of an inspection system for testing tubular products. A transmitter printed circuit meander coil with a wear surface covering was placed next to the part or workpiece 40 to be tested. A 0.0005" thick layer of high resistivity metal 14 was placed above the transmitter coil 10. A thin (0.0005" thick) layer of Kapton® insulation (not shown) was used to insulate the coil from the shield layer. Next, an identical insulated receiver coil 12 was placed above the shield layer shifted over ¼ wavelength as shown in FIG. 1. The shield layer was electrically connected to the preamp common 16. The new design performed very well. The reflection from an EDM (electro-discharge-machined) notch in a pipe sample 40 was clearly evident in a display of the testing electronics. The electronics has a circuit to blank the main bang from the receiver output. The duration of this blanking is set by the Main Bang Blanking setting in a transmitter electronics control screen of the testing device. The main bang was blanked completely out using a setting of 11 microseconds. This allowed the reflection from the notch in the pipe sample to be easily detected. In addition, the metal layer under the receiver coil serves to shield the receiver coil from electromagnetic noise. This EMAT coil design has been used in a steel mill with good results. Electromagnetic noise was eliminated and the short main bang has allowed the system to function adequately on tube samples with wall thickness as small as 0.150".

Typical main bang duration was known from previous setups. In this case, the same coil is used for transmitting and for receiving. A cable approx. 3' long was used between the EMAT coil and the transmitter matching network/preamp. The display showed the reflection from edges of a plate using a surface wave coil. It was necessary to use a main bang blanking setting of 22 microseconds to blank the main bang.

According to the invention, the duration of the main bang and hence the inspection dead zone created by the main bang can be significantly reduced for EMATs by:

1. Using separate coils for the transmitter and the receiver.
2. Shielding the receiver preamp from the transmitter matching electronics.
3. Offsetting the receiver coil from the transmitter coil by ¼ wavelength (where applicable).
4. Tuning the EMAT coil by placing the tuning capacitor as close as possible to the EMAT coil and connecting it with a short run of stripline cable.

The same techniques are also effective for spiral coil EMATs except it is not possible to offset the receiver coil by ¼ wavelength from the transmitter coil in such a case.

These techniques for minimizing the duration of the main bang have proven to be very effective. These techniques for main bang reduction have been incorporated in a system designed for inspecting tubular goods. The main bang reduction has resulted in excellent flaw detection capability in tubes with wall thickness as thin as 0.150". The invention is also being incorporated in a system being developed for the detection of corrosion fatigue cracking in boiler tubes. The reduction in main bang will result in the ability to detect cracks originating from the membrane weld using an EMAT adjacent to the membrane. All new EMAT designs should incorporate the inventive technique where possible.

While a specific embodiment of the invention has been shown and described in detail to illustrate the application of the principles of the invention, it will be understood that the invention may be embodied otherwise without departing from such principles.

We claim:

1. An EMAT arrangement with reduced main bang recovery time, comprising:
    a transmitter EMAT coil having a plurality of sections which are separated by a pitch distance;
    a receiver EMAT coil adjacent the transmitting coil, the receiving coil having a plurality of sections which are separated by a pitch distance, the coils being offset from each other by one half the pitch distance; and
    means for resistively shielding the transmitter coil from the receiver coil.

2. The EMAT arrangement according to claim 1, comprising electronics connected between said coils, said electronics having an output for supplying a signal to the transmitter coil and an inlet for receiving a signal from the receiver coil, a preamplifier connected between the receiver coil and the EMAT electronics input and a matching network connected between the output of the EMAT electronics and the transmitter coil.

3. The EMAT arrangement according to claim 1, further comprising a tuning capacitor and a stripline cable having first and second conductors and an insulating layer between said conductors, said first conductor being connected between one end of the transmitter coil and the receiver coil and one end of the tuning capacitor, and said second conductor being connected between an opposite end of said coils and an opposite end of said tuning capacitor.

4. An EMAT arrangement according to claim 1, wherein the means for resistively shielding comprises a thin, high resistivity metal shield.

5. An EMAT arrangement with reduced main bang recovery time, comprising:
    a transmitter EMAT coil having a plurality of sections which are separated by a pitch distance;
    means for applying a signal to said transmitter coil for transmitting a wave to a work piece, the wave having a wavelength;
    a receiver EMAT coil adjacent the transmitting coil for receiving a reflected wave from the work piece, the receiving coil having a plurality of sections which are separated by a pitch distance, the coils being offset from each other by one quarter of the wavelength; and
    means for resistively shielding the transmitter coil from the receiver coil.

6. An EMAT arrangement according to claim 5, wherein the means for resistively shielding comprises a thin, high resistivity metal shield.

* * * * *